(12) United States Patent
Zhang et al.

(10) Patent No.: US 9,902,693 B2
(45) Date of Patent: Feb. 27, 2018

(54) PREPARATION METHOD FOR PYRROLIDINE-2-CARBOXYLIC ACID DERIVATIVES

(71) Applicant: Zhejiang Jiuzhou Pharmaceutical Co., Ltd., Taizhou (CN)

(72) Inventors: Bin Zhang, Taizhou (CN); Yuanqiang Li, Taizhou (CN); Daqing Che, Taizhou (CN); Lingfeng Qian, Taizhou (CN); Guoliang Zhu, Taizhou (CN); Wenfa Ye, Taizhou (CN)

(73) Assignee: Zhejiang Jiuzhou Pharmaceutical Co., Ltd., Taizhou, Zhejiang (CN)

( * ) Notice: Subject to any disclaimer, the term of this patent is extended or adjusted under 35 U.S.C. 154(b) by 0 days.

(21) Appl. No.: 14/898,465

(22) PCT Filed: Jun. 23, 2014

(86) PCT No.: PCT/CN2014/080520
§ 371 (c)(1),
(2) Date: Dec. 14, 2015

(87) PCT Pub. No.: WO2014/206257
PCT Pub. Date: Dec. 31, 2014

(65) Prior Publication Data
US 2016/0145208 A1   May 26, 2016

(30) Foreign Application Priority Data

Jun. 26, 2013  (CN) .......................... 2013 1 0261857
Nov. 19, 2013  (CN) .......................... 2013 1 0580894
Jun. 10, 2014  (CN) .......................... 2014 1 0255311

(51) Int. Cl.
C07D 207/22   (2006.01)
C07D 207/16   (2006.01)

(52) U.S. Cl.
CPC ......... C07D 207/22 (2013.01); C07D 207/16 (2013.01); *Y02P 20/55* (2015.11)

(58) Field of Classification Search
USPC ...................................................... 548/533
See application file for complete search history.

(56) References Cited

FOREIGN PATENT DOCUMENTS

WO   2005073186 A1   8/2005
WO   2006073167 A1   7/2006

OTHER PUBLICATIONS

Takashi Kondo et al. Bioorganic & Medicinal Chemistry (2007), 15(7), 2631-2650.*
Takashi Kondo et al. Bioorganic & Medicinal Chemistry (2008), 16(1), 190-208 ("Kondo II").*
Greene Protective Groups in Organic Synthesis, 4th Edition (2006) Wiley Online Library, Chapter 7, Protection for the amino group, pp. 706-926, especially subsection "Protection for Imidazoles, Pyrroles, Indoles" at pp. 872-893 available at: http://onlinelibrary.wiley.com/doi/10.1002/9780470053485.ch7/pdf.*
Vedejs et al. J. Org. Chem., vol. 53(9) (1988), pp. 1876-1882.*
Jones et al., Tetrahedron Letters, vol. 31(16), pp. 2333-2336 (1990).*

* cited by examiner

*Primary Examiner* — Kamal Saeed

(57) ABSTRACT

The present invention relates to the field of medical synthesis, in particular to a preparation method for pyrrolidine-2-carboxylic acid derivatives. The present invention adopts the following technical solution: providing a compound having a structure of formula (E), wherein R is $R_1$ or $R_2$, $R_1$ is $C_1$-$C_6$ an alkyl, benzyl, p-methoxybenzyl, or p-nitrobenzyl group, and $R_2$ is hydrogen; $R_3$ is a protecting group of the carboxyl group; and $P_1$ is a protecting group on nitrogen.

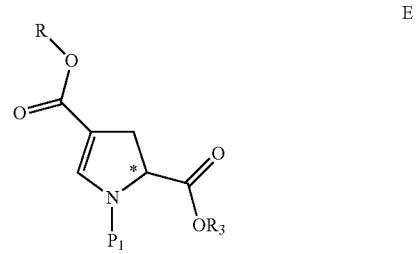

17 Claims, No Drawings

PREPARATION METHOD FOR PYRROLIDINE-2-CARBOXYLIC ACID DERIVATIVES

This application is a national stage application based on PCT/CN2014/080520, filed on Jun. 23, 2014, which claims the priority of China Patent Application No. 201310261857.4, 201310580894.1 and 201410255311.2 filed with the Patent Office of China on Jun. 26, 2013, Nov. 19, 2013 and Jun. 10, 2014 successively titled "Preparation method for pyrrolidine-2-carboxylic acid derivatives", the contents of which are incorporated herein by reference in their entirety.

FIELD OF THE INVENTION

The present invention relates to the field of medical synthesis, in particular to a preparation method for pyrrolidine-2-carboxylic acid derivatives.

BACKGROUND OF THE INVENTION

The following compound Z is the most common intermediate used in the field of medical synthesis,

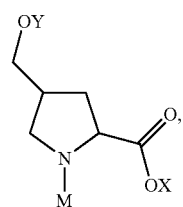

Wherein Y is a hydrogen atom or $C_1 \sim C_6$ alkyl.
M is a hydrogen atom or a protecting group on nitrogen.
X is a hydrogen atom or a protecting group of carboxyl.

Currently, there are a limited number of routes for preparing the above-mentioned compound, in which the yields are mostly low and the starting material is difficult to be produced.

When Y is a hydrogen atom, M is t-butyloxycarboryl (Boc), and X is methyl, compound Z has the following structure of formula Z-1,

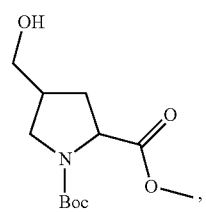

The PCT patent application No. WO2009118759 disclosed a method for preparing compound Z-1, which can be summarized as follows:

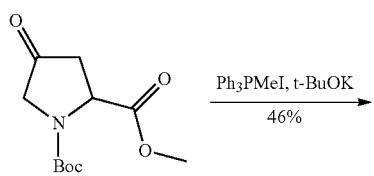

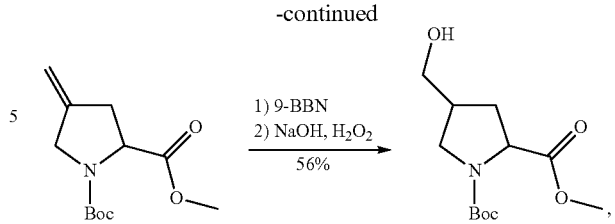

Wherein 9-BBN is abbreviation for 9-Borabicyclo[3.3.1] nonane, the yield is 46% in the first step, and it's 56% in the second step.

When Y is a hydrogen atom, M is t-butyloxycarbonyl (Boc), and X is tert-butyl, the said compound is represented by the following formula:

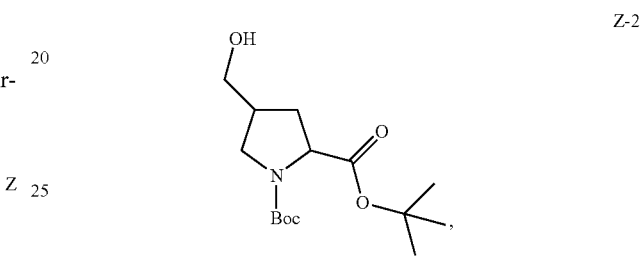

The same route for preparing the above-mentioned compound was disclosed in both Bioorganic & Medicinal Chemistry Letters, 21, (12), 3771-3773, 2011 and PCT patent application No. WO2004039367, which can be summarized as follows:

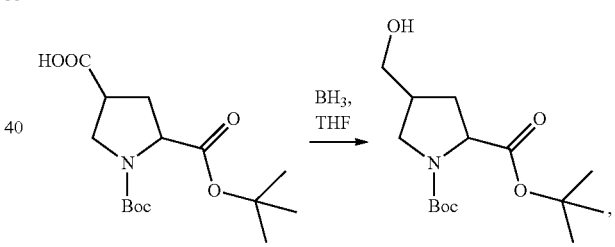

The yield is 41% in Bioorganic & Medicinal Chemistry Letters, 21, (12), 3771-3773, 2011, and 27% in WO2004039367.

When Y is methyl, M is t-butyloxycarboryl and X is methyl, the said compound can be represented by formula Z-3. When Y is methyl, M is t-butyloxycarboryl (Boc) and X is a hydrogen atom, the compound has the structure of formula Z-4:

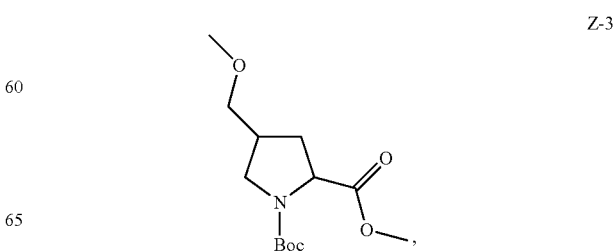

-continued

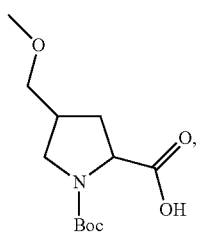
Z-4

PCT patent application with publication No. WO 2012068234 disclosed the following method for preparing the two aforesaid compounds on page 876.

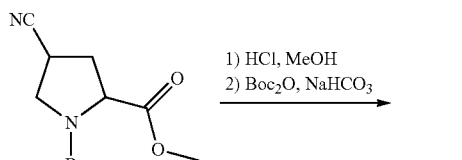

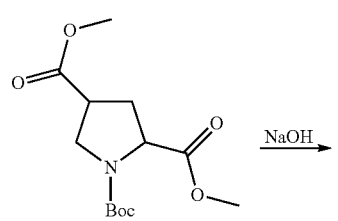

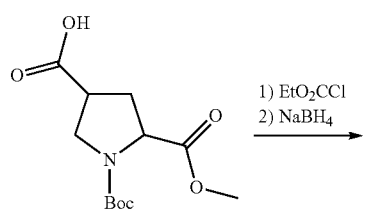

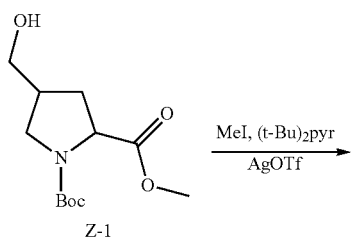

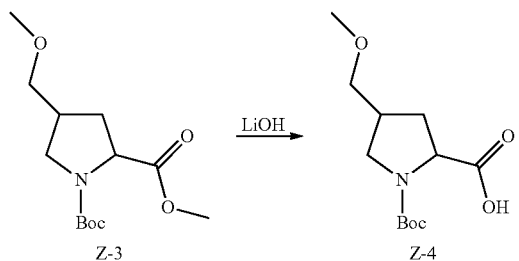

The above-mentioned methods are difficult to realize commercial production due to the use of high toxicity chemical such as 9-BBN, borane and sodium cyanide etc.,  and difficult operation processes. Therefore, it is necessary to provide novel methods to prepare the compound of formula Z.

SUMMARY OF THE INVENTION

The present invention adopts the following technical solution: providing a compound having a structure of formula E,

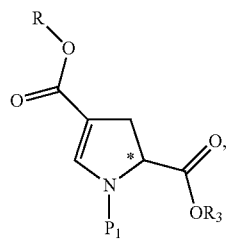
E wherein the position marked with * represents a chiral center, specifically, the configuration of carbon marked with * may be R, or may be S, or even may be the mixture of R and S.

Preferably, the compound E has the following configuration,

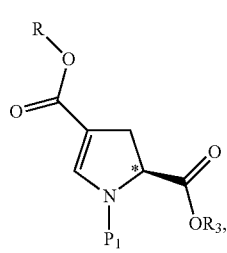
E

R is $R_1$ or $R_2$, $R_1$ is $C_1$~$C_6$ alkyl, benzyl, p-methoxybenzyl, p-nitrobenzyl, $R_2$ is a hydrogen atom;

$R_3$ is a protecting group for carboxyl;

$P_1$ is a protecting group of nitrogen.

Specifically, $R_1$ is methyl, ethyl, n-propyl, isopropyl, n-butyl, isobutyl, tert-butyl, n-amyl or n-hexyl;

$R_3$ is n-propyl, isopropyl, n-butyl, isobutyl, tert-butyl, n-amyl, n-hexyl, benzyl, triphenylmethyl, p-methoxybenzyl or p-nitrobenzyl.

$P_1$ is acetyl, trifluoroacetyl, allyloxycarbonyl, t-butyloxycarboryl(Boc), trimethylsilyl (TMS), tert-butyldimethylsilyl (TBDMS), benzoyl, triphenylmethyl, p-methoxybenzyl, benzyloxycarbonyl (Cbz), p-methoxybenzyloxycarbonyl (Moz), p-nitrobenzyl, m-nitrobenzyl, p-chlorobenzyl, m-chlorobenzyl, p-bromobenzyl, m-bromobenzyl or benzyl.

Preferably, $R_1$ is $C_1$~$C_6$ alkyl; $R_3$ is tert-butyl, benzyl, p-methoxybenzyl or p-nitrobenzyl; $P_1$ is t-butyloxycarbonyl, p-methoxybenzyl or carboxybenzyl.

More preferably, $R_1$ is methyl; $R_3$ is tert-butyl or benzyl; $P_1$ is t-butyloxycarbonyl.

Preferably, the compound E can be described by the compound of formula e1 when R is $R_1$:

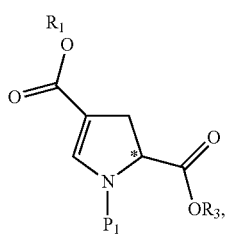

e1 wherein $R_1$, $R_3$ and $P_1$ are as defined above.

The compound of formula e1 is obtained from the compound of formula g and formic mixed anhydride or alkyl formate by cyclization reaction.

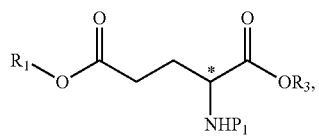

g wherein $R_3$, $R_1$ and $P_1$ are as defined above.

The cyclization reaction was performed in the presence of strong base which has the ability to remove a-H.

Further, the reaction yield can be improved by adding an acid.

The formic mixed anhydride can be selected from formic anhydride, acetic formic anhydride, formic pivalic anhydride and formic benzoic anhydride.

The alkyl formate can be selected from methyl formate, ethyl formate, propyl formate and isopropyl formate.

The strong base may be selected from lithium bis(trimethylsilyl)amide, lithium diisopropylamide, n-butyllithium, sodium hydride, sodium alcoholate and potassium alcoholate. The preferable sodium alcoholate may be selected from sodium methoxide, sodium ethoxide and sodium isopropylate; the preferable potassium alcoholate may be potassium methoxide, potassium ethoxide, potassium isopropoxide.

The acid may be trifluoroacetic acid or acetic acid.

The compound g was obtained by reacting the compound of formula h with $(R_3CO)_2$ or $R_3X$ in the presence of base,

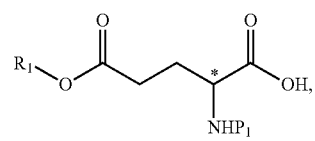

h wherein $R_1$, $R_3$ and $P_1$ is as defined above, X is a halogen atom, preferably Br or Cl.

The said base may be 4-(dimethylamino)pyridine (DMAP), triethylamine, pyridine, tetramethyl guanidine, 1,8-diazabicyclo[5.4.0]undec-7-ene (DBU), sodium carbonate, potassium carbonate or lithium carbonate.

The preferred solvent employed may include $R_3OH$, DMF, THF or acetonitrile.

The compound E can be represented by formula e1 when R is $R_1$,

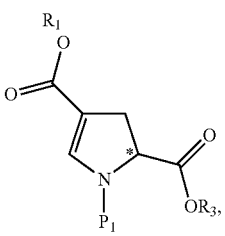

e1 wherein $R_1$, $R_3$ and $P_1$ is as defined above.

The compound E is represented by formula e2 when R is $R_2$ (a hydrogen atom).

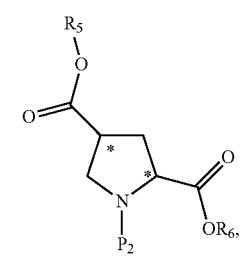

e2

In this case, the said compound of formula e1 is hydrolyzed to generate the compound of formula e2. The preferred reaction reagent for the hydrolysis may be alkali base, such as lithium hydroxide, sodium hydroxide, potassium hydroxide and so on.

In another aspect, the compound of formula E is subjected to catalytic hydrogenation to obtain the compound of formula D,

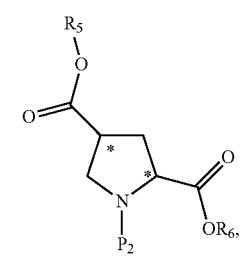

D wherein $R_5$ is a hydrogen atom or $C_1$~$C_6$ alkyl, the specific example is methyl, ethyl, n-propyl, isopropyl, n-butyl, isobutyl, tert-butyl, n-pentyl and n-hexyl.

$R_6$ is a hydrogen atom, n-propyl, isopropyl, n-butyl, isobutyl, tert-butyl, n-pentyl or n-hexyl.

$P_2$ is a hydrogen atom, acetyl, trifluoroacetyl, allyloxycarbonyl, t-butyloxycarboryl (Boc), trimethylsilyl (TMS), tert-butyldimethylsilyl (TBDMS) or benzoyl.

The catalyst for catalytic hydrogenation may be selected from palladium on carbon, platinum oxide, Raney Ni as well as chiral catalyst.

The said chiral catalyst may be the compound represented by formula M1 or formula M2

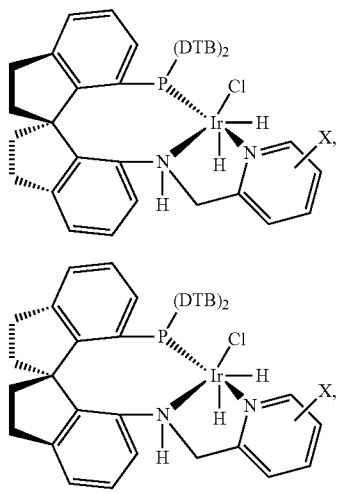

wherein DTB is

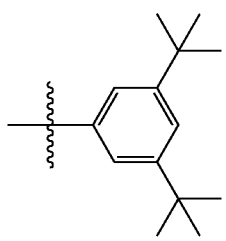 [SMILES: *c1cc(C(C)(C)C)cc(C(C)(C)C)c1]

X is $C_1$~$C_4$ alkyl.

Furthermore, the compound of formula D is reduced to the compound of formula c1.

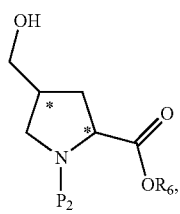

wherein $R_6$ and $P_2$ are as defined above.

The reducing agent employed in the process above may be tributyltin hydride, triphenyltin hydride, triethylsilicane, trichlorosilane, sodium borohydride, sodium trimethoxyborohydride, lithium tri-sec-butylhydridoborate, potassium Tri-Sec-Butylborohydride, lithium triethylborohydride, diisobutylaluminium hydride (DIBAH) or sodium bis(2-methoxyethoxy)aluminiumhydride; preferably, when $R_5$ of compound D is a hydrogen atom, the carboxyl group can be reduced to the hydroxy group under mild reaction condition with the decrease of the formation of impurities by the activation with the addition of alkyl chloroformate such as ClCOOEt, ClCOOMe and so on to generate a mixed acid anhydride first.

Racemization doesn't occur during the preparation of the compound of formula c1 from the compound of formula E according to the reduction steps described above if the compound of formula E is a single enantiomer of chiral compound, and only cis isomer of the compound of formula c1 is obtained.

Furthermore, the compound of formula c1 can convert to the compound of formula b1 by removal of the carboxyl group.

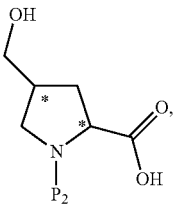

wherein $P_1$ and $P_2$ are as defined above.

The reagent employed in the process of removing the carboxyl group may be selected from formic acid, trifluoroacetic acid, hydrochloric acid, acetic acid and p-toluenesulfonic acid, etc.

The compound of formula b1 is subjected to alkylation to produce the compound of formula A1,

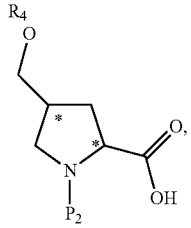

wherein $R_4$ is $C_1$~$C_6$ alkyl.

Alkylating reagent may be selected from iodomethane, bromoethane, dimethyl sulfate, diethyl sulfate, methyl methanesulfonate, methyl p-toluenesulfonate, methyl trifluoromethansulfonate, oxalic acid dimethyl ester and methyl carboxylate etc.

In order to improve the nucleophilicity of the hydroxy group of compound b1 or b2, the hydroxyl group may be activated with strong base such as metallic sodium, sodium hydride, n-butyllithium and so on to form the corresponding sodium alkoxide or lithium alkoxid, which reacts with alkylating reagent in the presence of phase transfer catalyst, for example, quaternary ammonium salt, polyethylene glycol and etc.

The compound of formula c1 is converted to the compound of formula A1 without racemization after the steps of removal the protecting group of carboxyl group and alkylation if it is a single enantiomer of chiral compound.

Alternatively, the compound of formula c1 can be converted to the compound of formula A1 directly by alkylation process.

The compound c1 is alkylated directly to give the compound A1 which will be racemizated if the carboxyl group in 2-position of compound c1 is a single chiral.

The present invention provides the preparation method for pyrrolidine-2-carboxylic acid derivatives and has advantages that the compound of formula D is obtained as cis isomer by the catalytic hydrogenation of double bond in the compound of formula E when the compound E is a single enantiomer of chiral compound. But in general, a person skilled in the art knows that the product is a racemic mixture when the double bond of alkene is subjected to catalytic hydrogenation. For example, the compound of formula N which has a similar structure as the compound provided by the present invention undergoes catalytic hydrogenation to produce a product with racemization at 4 position (see comparison example 1). This has not been clearly indicated in common knowledge. Therefore, the compound E provided by the present invention has achieved an unexpected technical effect.

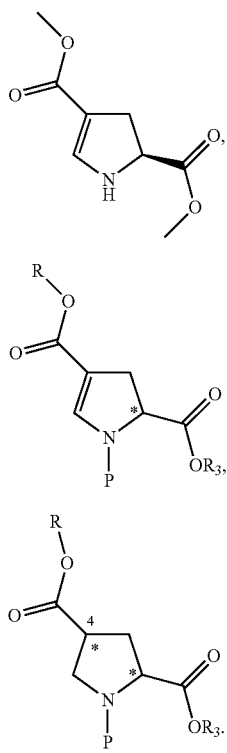

N

E

D

The method also has the advantages of cheap raw materials, simple operation, mild conditions, and effectively decreases the production cost.

DETAILED EMBODIMENTS

EXAMPLE 1

The Preparation of 1-tert-butyl-5-methyl-2-((tert-butyloxycarbonyl)amino)pentanedioate

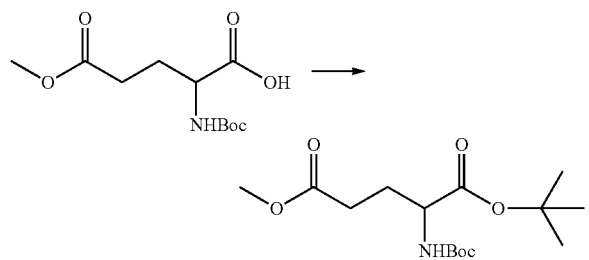

To a 100 ml one-necked flask was added 5-methyl-2-((tert-butyloxycarbonyl)amino)-pentanedioate (7.8 g, 24.6 mmol), di-tert-butyl dicarbonate (5.9 g, 27 mmol), 4-dimethylaminopyridine (0.9 g, 7.38 mmol) and 30 ml tertiary butanol. After the mixture was stirred at 25° C. overnight, the solvent was evaporated and the residue was purified by column chromatography to afford 7.17 g 1-tert-butyl-5-methyl-2-((tert-butyloxycarbonyl)amino)pentanedioate as white solid with a yield of 91.9%.

EXAMPLE 2

The Preparation of 1-benzyl-5-methyl-2-((tert-butyloxycarbonyl)amino)pentanedioate

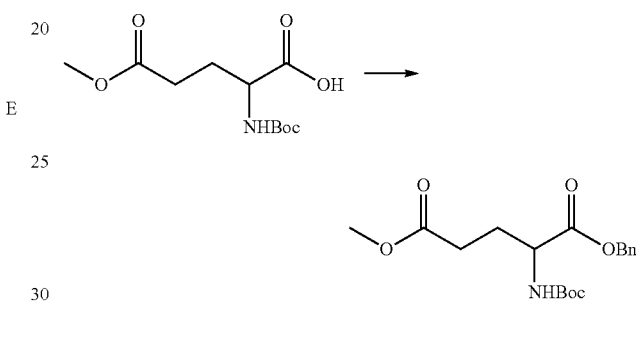

To a 100 ml one-necked flask was added 5-methyl-2-((tert-butyloxycarbonyl)amino)-pentanedioate (7.8 g, 24.6 mmol), di-benzyl dicarbonate (6.86 g, 27 mmol), triethylamine (0.75 g, 7.4 mmol) and 30 ml methanol. After the mixture was stirred at 30° C. for one night, the solvent was evaporated and the residue was purified by column chromatography to afford 7.1 g 1-benzyl-5-methyl-2-((tert-butyloxycarbonyl)amino)pentanedioate as white solid with a yield of 82.3%.

EXAMPLE 3

The Preparation of 1-tert-butyl-5-methyl-2-acetamino pentanedioate

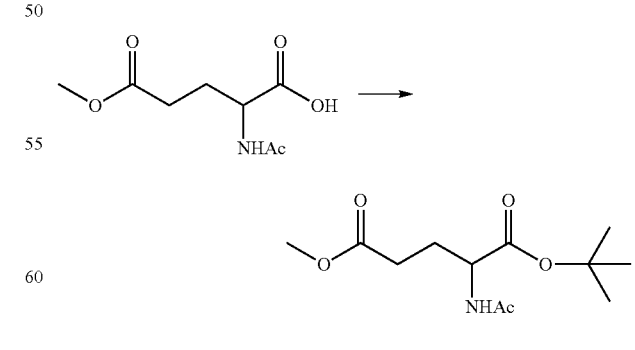

The procedure of example 1 was repeated by using 5 g 5-methyl-2-acetamino pentanedioate as starting material to obtain 5.5 g 1-tert-butyl-5-methyl-2-acetamino pentanedioate with a yield of 86.6%.

EXAMPLE 4

The Preparation of (S)-1-tert-butyl-5-methyl-2-benzyloxycarbonylamino pentanedioate

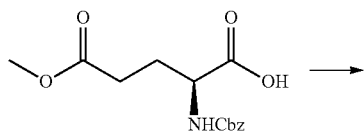

The procedure of example 1 was repeated by using 2.95 g 5-methyl-2-benzyloxycarbonylaminopentanedioate as starting material to obtain 3.5 g with a yield of 99%.

EXAMPLE 5

The Preparation of N-t-butyloxycarbonyl-2-t-butyloxycarbonyl-4-methoxycarbonyl-2,3-dihydro-1H-pyrrole

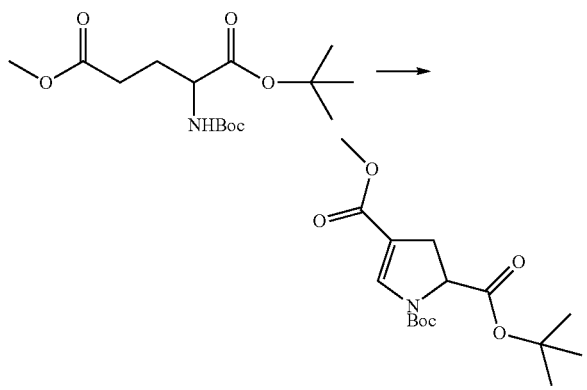

60 ml lithium bis(trimethylsilyl)amide (7.6 g, 45.4 mmol) was charged into a 250 ml three-necked flask under the protection of nitrogen and cooled to −78° C. A solution of 1-t-butyl-5-methyl-2-((t-butyloxycarbonyl)amino)pentanedioate (8.0 g, 25.2 mmol) in 20 ml THF was added dropwise. After the addition, the mixture was maintained at −78° C. for 1 h. A solution of acetic formic anhydride (2M, 40 mmol) in 20 ml THF was added dropwise slowly. The inner temperature was maintained below −70° C. After the addition, the mixture was maintained at −78° C. for 3 h, then heated to 5° C. The resulting mixture was quenched with 4.0 ml of acetic acid and 30 ml of water, extracted with ethyl acetate and the combined organic phase was dried over MgSO$_4$, filtered and concentrated to give a light yellow oil. Then the above mentioned oil was dissolved in methylene chloride, cooled to 5° C., after the addition of TFA (3.16 g, 27.7 mmol), the mixture was stirred for 4 hours at 25° C., concentrated and purified by column chromatography to afford 6.8 g N-t-butyloxycarbonyl-2-t-butyloxycarbonyl-4-methoxycarbonyl-2,3-dihydro-1H-pyrrole as white solid with a yield of 82.9%.

$^1$HNMR (400 Mz, CDCl$_3$): δ=1.48-1.49 (m, 18H), δ=2.80-2.87 (m, 1H), δ=3.15-3.28 ( m, 1H ), δ=4.56-4.67 (m, 1H), δ=7.42-7.58 (d, 1H).

EXAMPLE 6

The Preparation of N-tert-butoxycarbonyl-2-tert-butoxycarbonyl-4-methoxycarbonyl-2,3-dihydro-1H-pyrrole

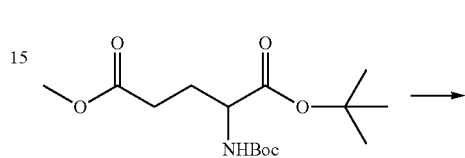

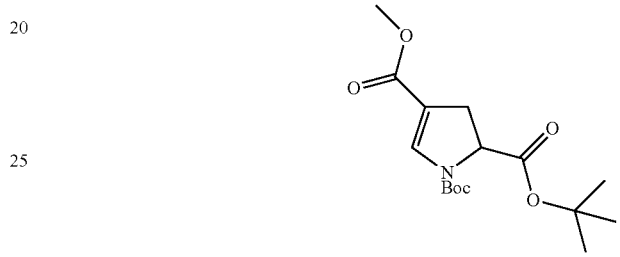

To a 250 ml of three-necked bottle was added 60 ml of LHMDS (7.6 g, 45.4 mmol) with the protection of nitrogen, then cooled to −78° C., after the addition of a solution of 1-tert-butyl 5-methyl 2-((tert-butoxycarbonyl)amino)pentanedioate (8.8 g, 27.8 mmol) in 20 ml THF, the mixture was stirred for another 1 hour at −78° C., then a solution of acetic formic anhydride in 20 ml of THF was added dropwise to maintain the inner temperature below −70° C. After addition, the mixture was stirred for another 3 hours at −78° C., the reaction solution was warmed to 5° C., then quenched the reaction with 4.0 ml of acetic acid and 30 ml of water, extracted with ethyl acetate and combined the organic phase then dried over MgSO$_4$, filtered and concentrated to give a light yellow oil. Then the above mentioned oil was dissolved in methylene chloride, cooled to 5° C., after the addition of TFA (3.16 g, 27.7 mmol), the mixture was stirred for 4 hours at 25° C., after the addition of 40 ml water, then concentrated, and extracted with DCM (50 ml×3), combined the organic phase and evaporated to dryness to give 8.7 g of N-tert-butoxycarbonyl-2-tert-butoxycarbonyl-4-methoxycarbonyl-2,3-dihydro-1H-pyrrole in 95.7% yield.

EXAMPLE 7

The Preparation of (S)-N-acetyl-2-tert-butoxycarbonyl-4-metboxycarbonyl-2,3-dihydro-1H-pyrrole

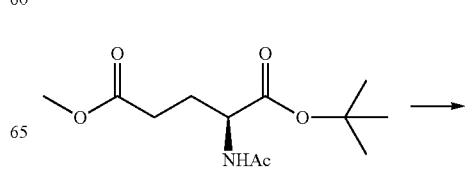

-continued

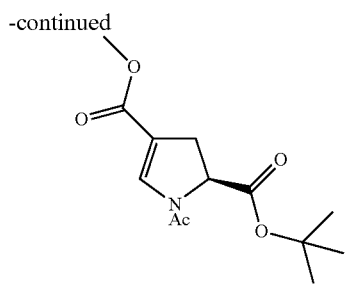

To a 250 ml of three-necked bottle was added a solution of 25 ml ″BuLi in hexane (1.6M, 40 mmol) under the protection of nitrogen, then cooled to −78° C., after the addition of the solution of (S)-1-tert-butyl-5-methyl-2-acetamino pentanedioate (6.5 g, 25.1 mmol) in 20 ml THF, the mixture was stirred for another 1 hour at −78° C., then a solution of formic pivalic anhydride in 20 ml of THF (2M, 40 mmol) was added dropwise slowly to maintain the inner temperature below −70° C., after the addition, stirred at −78° C. for 3 hours, and warmed to 5° C., then quenched with 4.0 ml of acetic acid and 30 ml of water, extracted with ethyl acetate. The combined organic phase was dried over MgSO$_4$, filtered and concentrated to give a light yellow oil. Then the above mentioned oil was dissolved in methylene chloride, cooled to 5° C., after the addition of TFA (3.16 g, 27.7 mmol), the mixture was stirred for 4 hours at 25° C., then concentrated, and then purified by column chromatography to give 5.7 g of (S)-N-acetyl-2-tert-butoxycarbonyl-4-methoxycarbonyl-2,3-dihydro-1H-pyrrole in 84.4% yield.

EXAMPLE 7-2

The preparation of (S)-N-acetyl-2-tert-butoxycarbonyl-4-methoxycarbonyl-2,3-dibydro-1H-pyrrole

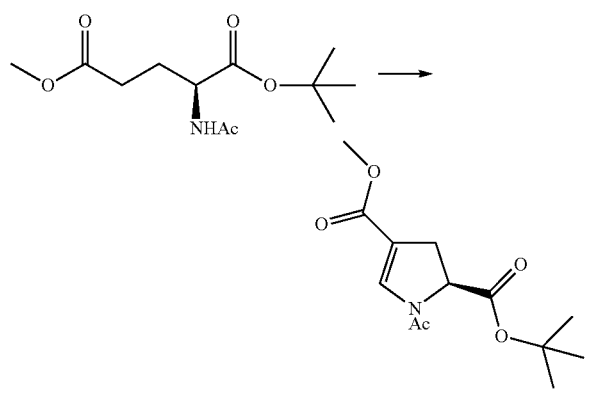

To a 250 m of three-necked bottle was added a solution of 25 ml ″BuLi in hexane (1.6M, 40 mmol) under the protection of nitrogen, then cooled to −78° C., after the addition of the solution of (S)-1-tert-butyl-5-methyl-2-acetamino pentanedioate (6.5 g, 25.1 mmol) in 20 ml THF, the mixture was stirred for another 1 hour at −78° C., then a solution of formic pivalic anhydride in 20 ml of THF (2M, 40 mmol) was added dropwise slowly to maintain the inner temperature below −70° C., after the addition, stirred at −78° C. for 3 hours, and warmed to ° C., then quenched with 4.0 ml of acetic acid and 30 ml of water, extracted with ethyl acetate. The combined organic phase was dried over MgSO$_4$, filtered and concentrated to give a light yellow oil. Then the above mentioned oil was dissolved in methylene chloride, cooled to 5° C., after the addition of TFA (3.16 g, 27.7 mmol), the mixture was stirred for 4 hours at 25° C., then concentrated, after the addition of 40 ml water, extracted with DCM (3×50 ml),), then purified by column chromatography to give 6.1 g of (S)-N-acetyl-2-tert-butoxycarbonyl-4-methoxycarbonyl-2,3-dihydro-1H-pyrrole in 90.5% yield.

EXAMPLE 8

The Preparation of (R)-N-trimethylsilyl-2-tert-butoxycarbonyl-4-isopropoxycarbonyl-2,3-dihydro-1H-pyrrole

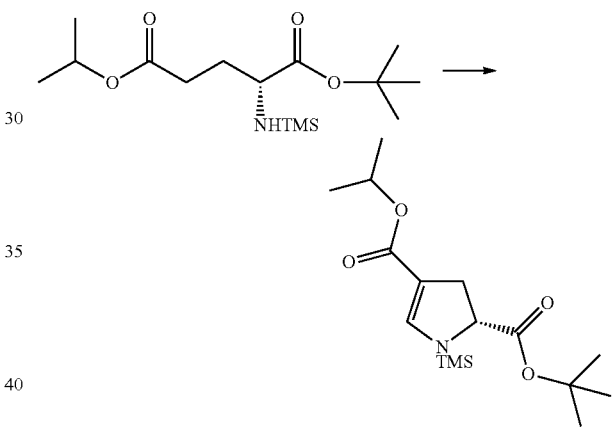

To a 250 ml of three-necked bottle was added LDA (3.0 g, 28 mmol) with the protection of nitrogen, then cooled to −78° C., after the addition of (R)-1-tert-butyl-5-isopropyl 2-((trimethylsilyl)amino)pentanedioate (4.8 g, 15.1 mmol) (prepared according to Example 1) in 15 ml of THF, the mixture was stirred for another 1.5 hours at −78° C., then a solution of formic acetic anhydride in 12 ml of THF (2M, 24 mmol) was added dropwise slowly to maintain the inner temperature below −70° C., after addition, stirred for another 4 hours at −78° C., the reaction solution was warmed to 5° C., then quenched the reaction with 3.0 ml of acetic acid and 20 ml of water, extracted with ethyl acetate and the combined organic phase was dried over MgSO$_4$, filtered and concentrated to give a light yellow oil. Then the above mentioned oil was dissolved in methylene chloride, cooled to 5° C., after the addition of TFA (3.16 g, 27.7 mmol), the mixture was stirred for 4 hours at 25° C., then concentrated, purified by column chromatography to give 3.74 g of (R)-N-trimethylsilyl-2-tert-butoxycarbonyl-4-isopropoxycarbonyl-2,3-dihydro-1H-pyrrole in 75.6% yield.

EXAMPLE 9

The Preparation of (S)-N-tert-butoxycarbonyl-2-tert-butoxycarbonyl-4-carboxyl-2,3-dihydro-1H-pyrrole

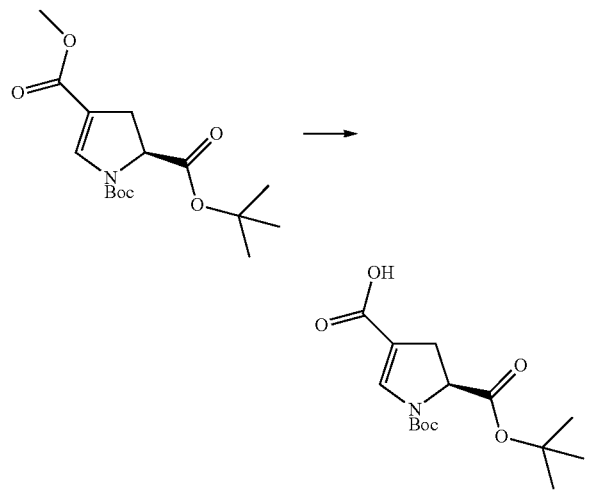

To a 100 ml of single-necked bottle was added (S)-N-tert-butoxycarbonyl-2-tert-butoxycarbonyl-4-methoxycarbonyl-2,3-dihydro-1H-pyrrole (3.2 g, 10 mmol) (prepared by the method of Example 5), LiOH (0.63 g, 15 mmol), 15 ml of water and 15 ml of THF, then the mixture was stirred at 25° C. overnight, extracted with ethyl acetate to remove the organic impurities, the aqueous phase was adjust to PH=3, then extracted with ethyl acetate (3×15 ml), dried over MgSO$_4$, filtrated and evaporated to afford 3.1 g of (S)-N-tert-butoxycarbonyl-2-tert-butoxycarbonyl-4-carboxyl-2,3-dihydro-1H-pyrrole in 100% yield.

$^1$HNMR (400 Mz, CDCl$_3$): δ=1.49-1.53 (m, 18H), δ=2.83-2.86 (m, 1H), δ=3.16-3.29 ( m, 1H ), δ=4.59-4.70 (m, 1H), δ=7.54-7.72 (d, 1H).

EXAMPLE 10

The Preparation of (2S,4S)-N-tert-butoxycarbonyl-2-tert-butoxycarbony-4-methoxycarbonyl pyrrolidine

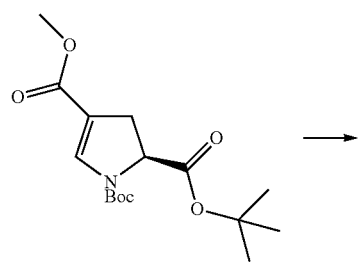

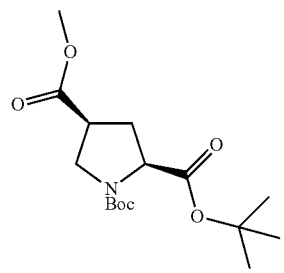

To a 100 ml of single-necked bottle was added (S)-N-tert-butoxycarbonyl-2-tert-butoxycarbonyl-4-methoxycarbonyl-2,3-dihydro-1H-pyrrole (3.27 g, 10 mmol) (prepared by the method of Example 5), 10% wet Pd/C (0.7 g, 30%), one drop of acetic acid and 5 ml of methanol, then the mixture was stirred at 25° C. overnight, after filtration and evaporation, 3.3 g of (2S,4S)-N-tert-butoxycarbonyl-2-tert-butoxycarbony-4-methoxycarbonyl pyrrolidine was obtained in 100% yield, de 99%.

$^1$HNMR (400 Mz, CDCl$_3$): δ=1.42-1.45 (m, 18H), δ=2.26-2.34 (m, 1H), δ=2.46-2.51 ( m, 1H ), δ=3.00-3.07 (m, 1H), δ=3.69 (s, 3H), δ=3.69-3.86 (m, 1H), δ=4.12-4.20 (m, 1H).

EXAMPLE 11

The Preparation of (2S,4S)-N-acetyl-2-tert-butoxycarbonyl-4-methoxycarbonyl pyrrolidine

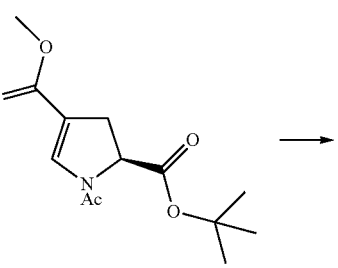

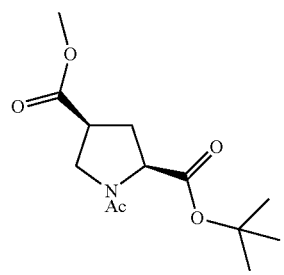

To a 100 ml of single-necked bottle was added (S)-N-acetyl-2-tert-butoxycarbonyl-4-methoxycarbonyl-2,3-dihydro-H-pyrrole (2.7 g, 10 mmol), 10% wet Pd/C (0.7 g, 30%), one drop of acetic acid and 5 ml of methanol, then the mixture was stirred at 25° C. overnight, after filtration and evaporation, 2.7 g of (2S,4S)-N-acetyl-2-tert-butoxycarbonyl-4-methoxycarbonyl pyrrolidine was obtained in 100% yield, de 97.5%.

EXAMPLE 11-2

The Preparation of (2S,4S)-N-acetyl-2-tert-butoxycarbonyl-4-methoxycarbonyl pyrrolidine

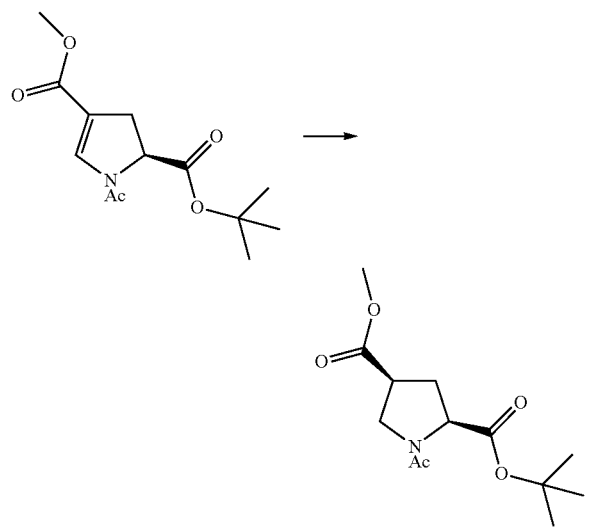

To a 100 ml of single-necked bottle was added (S)-N-acetyl-2-tert-butoxycarbonyl-4-methoxycarbonyl-2,3-dihydro-1H-pyrrole (2.7 g, 10 mmol), 0.3 g of Raney nickel, one drop of acetic acid and 5 ml of methanol, then the mixture was stirred at 25° C. overnight, after filtration and evaporation, 2.7 g of (2S,4S)-N-acetyl-2-tert-butoxycarbonyl-4-methoxycarbonyl pyrrolidine as colourless oil was obtained in 100% yield, de 97.6%.

EXAMPLE 12

The Preparation of (2R,4R)-N-(trimethylsilyl)-2,4-di(tert-butoxycarbonyl) pyrrolidine

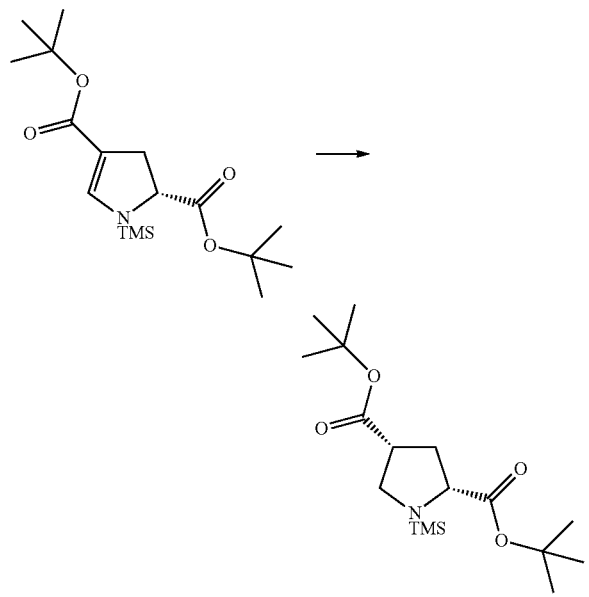

To a 100 ml of single-necked bottle was added (R)-N-(trimethylsilyl)-2,4-di(tert-butoxycarbonyl)-2,3-dihydro-1H-pyrrole (3.4 g, 10 mmol), 10% wet Pd/C (0.7 g, 30%) and 5 ml of methanol, then the mixture was stirred at 25° C. overnight, after filtration and evaporation, 3.4 g of (2R,4R)-N-(trimethylsilyl)-2,4-di(tert-butoxycarbonyl)pyrrolidine as colourless oil was obtained in 99% yield, de 98%.

EXAMPLE 13

The Preparation of (2S,4S)-2-carboxyl-4-(ethoxycarbonyl) pyrrolidine

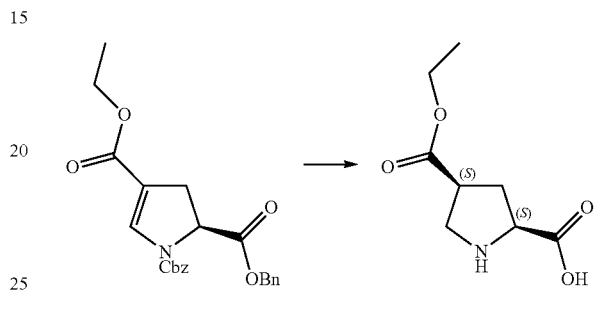

To a 100 ml of single-necked bottle was added (S)-N-benzyloxycarbonyl-2-benzyloxycarbonyl-4-ethoxycarbonyl-2,3-dihydro-1H-pyrrole (4.0 g, 10 mmol) (obtained according the example 5), 10% wet Pd/C (0.7 g, 30%), one drop of acetic acid and 5 ml of methanol, then the mixture was stirred at 25° C. overnight after filtration and evaporation, 4 g of (2S,4S)-2-carboxyl-4-(ethoxycarbonyl) pyrrolidine was obtained in 100% yield, de 98.7%.

EXAMPLE 14

The Preparation of (S)-N-tert-butoxycarbonyl-2-benzyloxycarbonyl-4-ethoxycarbonyl-2,3-dihydro-1H-pyrrole

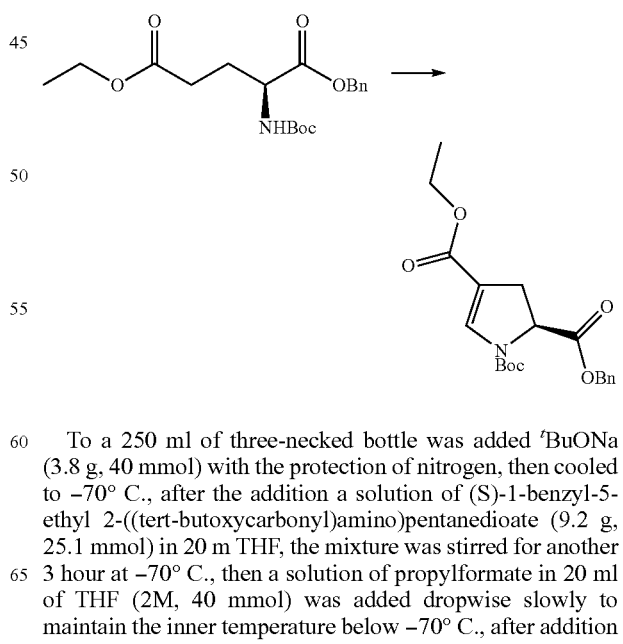

To a 250 ml of three-necked bottle was added ᵗBuONa (3.8 g, 40 mmol) with the protection of nitrogen, then cooled to −70° C., after the addition a solution of (S)-1-benzyl-5-ethyl 2-((tert-butoxycarbonyl)amino)pentanedioate (9.2 g, 25.1 mmol) in 20 m THF, the mixture was stirred for another 3 hour at −70° C., then a solution of propylformate in 20 ml of THF (2M, 40 mmol) was added dropwise slowly to maintain the inner temperature below −70° C., after addition and maintained at −70° C. for another 5 hours. The reaction solution was warmed to 5° C., then quenched the reaction with 4.0 ml of acetic acid and 30 ml of water, extracted with ethyl acetate, dried over MgSO₄, filtered and concentrated to give a light yellow oil. Then the above mentioned oil was dissolved in methylene chloride, cooled to 5° C., after the addition of TFA (3.16 g, 27.7 mmol), the mixture was warmed to for 25° C. with stirring for 4 hours, then concentrated, after 40 ml of water was added and extracted with DCM (50×3) to give 9 g of N-tert-butoxycarbonyl-2-benzyloxycarbonyl-4-ethoxycarbonyl-2,3-dihydro-1H-pyrrole in 95.7% yield. ee 98.3%.

EXAMPLE 15

The Preparation of (2S,4S)-N-tert-butoxycarbonyl-2-tert-butoxycarbonyl-4-carboxyl pyrrolidine

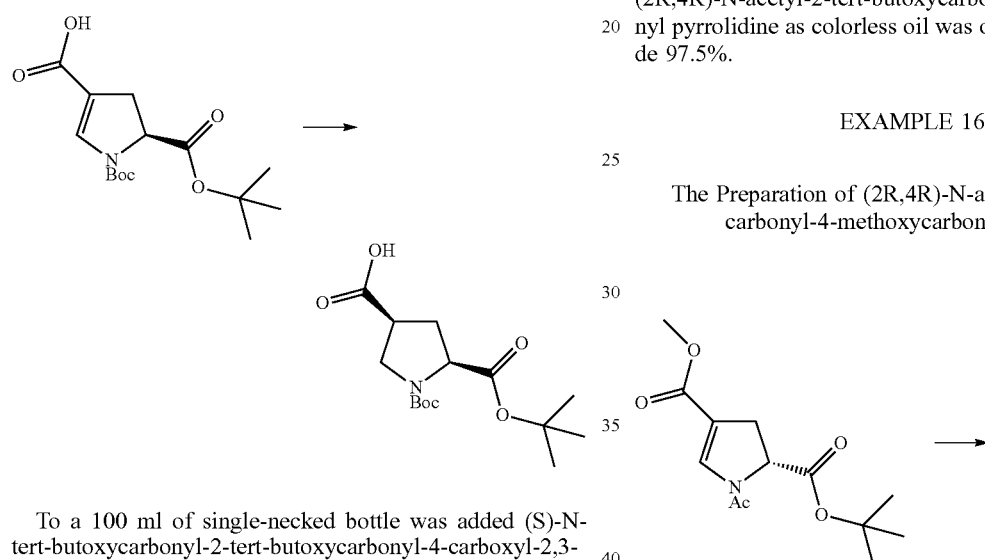

To a 100 ml of single-necked bottle was added (S)-N-tert-butoxycarbonyl-2-tert-butoxycarbonyl-4-carboxyl-2,3-dihydro-1H-pyrrole (3.13 g, 10 mmol), 10% wet Pd/C (0.7 g, 30%), one drop of acetic acid and 5 ml of methanol, then the mixture was stirred at 25° C. overnight, after filtration and evaporation, 3.158 g of (2S,4S)-N-tert-butoxycarbonyl-2-tert-butoxycarbonyl-4-carboxyl pyrrolidine was obtained in 100% yield, de 98.8%.

¹HNMR (400 Mz, CDCl₃): δ=1.45-1.47 (m, 18H), δ=2.32-2.39 (m, 1H), δ=2.49-2.55 ( m, 1H ), δ=3.06-3.13 (m, 1H), δ=3.72-3.89 (m, 2H), δ=4.16-4.25 (m, 1H).

EXAMPLE 16

The Preparation of (2R,4R)-N-acetyl-2-tert-butoxycarbonyl-4-methoxycarbonylpyrrolidine

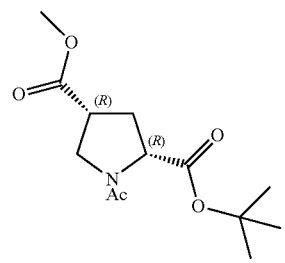

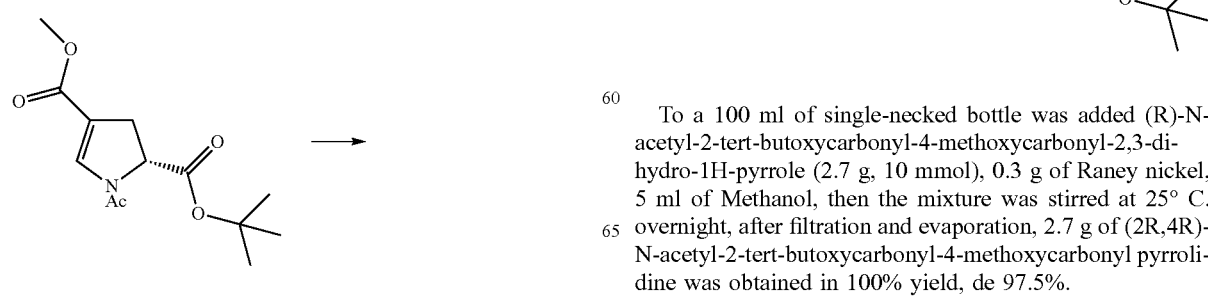

To a 100 ml of single-necked bottle was added (R)-N-acetyl-2-tert-butoxycarbonyl-4-methoxycarbonyl-2,3-dihydro-1H-pyrrole (2.7 g, 10 mmol), 10% wet Pd/C (0.7 g, 30%), 5 ml of Methanol, then the mixture was stirred at 25° C. overnight, after filtration and evaporation, 2.7 g of (2R,4R)-N-acetyl-2-tert-butoxycarbonyl-4-methoxycarbonyl pyrrolidine as colorless oil was obtained in 100% yield, de 97.5%.

EXAMPLE 16-2

The Preparation of (2R,4R)-N-acetyl-2-tert-butoxycarbonyl-4-methoxycarbonyl pyrrolidine To a 100 ml of single-necked bottle was added (R)-N-acetyl-2-tert-butoxycarbonyl-4-methoxycarbonyl-2,3-dihydro-1H-pyrrole (2.7 g, 10 mmol), 0.3 g of Raney nickel, 5 ml of Methanol, then the mixture was stirred at 25° C. overnight, after filtration and evaporation, 2.7 g of (2R,4R)-N-acetyl-2-tert-butoxycarbonyl-4-methoxycarbonyl pyrrolidine was obtained in 100% yield, de 97.5%.

EXAMPLE 17

The Preparation of (2S,4S)-N-tert-butoxycarbonyl-2-(p-methoxybenyloxy)carbonyl-4-hydroxymethyl-pyrrole

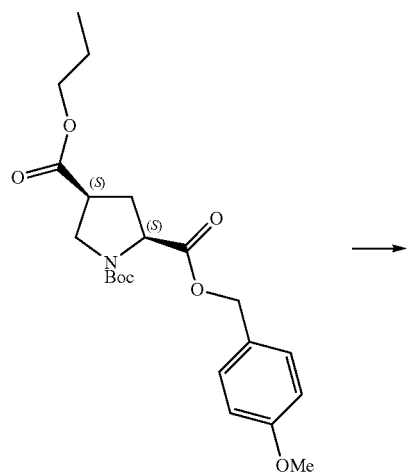

To a mixture of (2S,4S)-N-tert-butoxycarbonyl-2-(p-methoxybenyloxy)carbonyl-4-propoxy pyrrolidine (3 g, 8.26 mmol) in 20 ml of methanol was added diisobutylaluminium hydride (3.55 g, 25 mmol), then the mixture was stirred at 25° C. overnight, quenched by dilute HCl, extracted with ethyl acetate, then purified by column chromatography to give 2.45 g of (2S,4S)-N-tert-butoxycarbonyl-2-(p-methoxybenyloxy)carbonyl-4-hydroxymethylpyrrole in 81.2% yield, de 96.8%.

EXAMPLE 18

The Preparation of (2S,4S)-N-tert-butoxycarbonyl-2-tert-butoxycarbonyl-4-hydroxymethylpyrrolidine

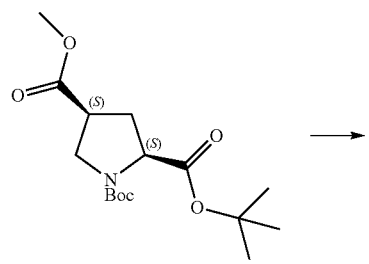

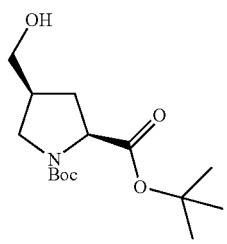

To a mixture of (2S,4S)-N-tert-butoxycarbonyl-2-tert-butoxycarbonyl-4-methoxycarbonyl pyrrolidine (2 g, 6.1 mmol) in 20 ml of isopropanol was added sodium borohydride (0.74 g, 20 mmol), then the mixture was stirred at 25° C. overnight, quenched by dilute HCl, extracted with ethyl acetate, then purified by column chromatography to give 1.5 g of (2S,4S)-N-tert-butoxycarbonyl-2-tert-butoxycarbonyl-4-hydroxymethylpyrrolidine as oil in 81.9% yield, de 81.9%.

EXAMPLE 18-2

The Preparation of (24S)-N-tert-butoxycarbonyl-2-tert-butoxycarbonyl-4-hydroxymethylpyrrolidine

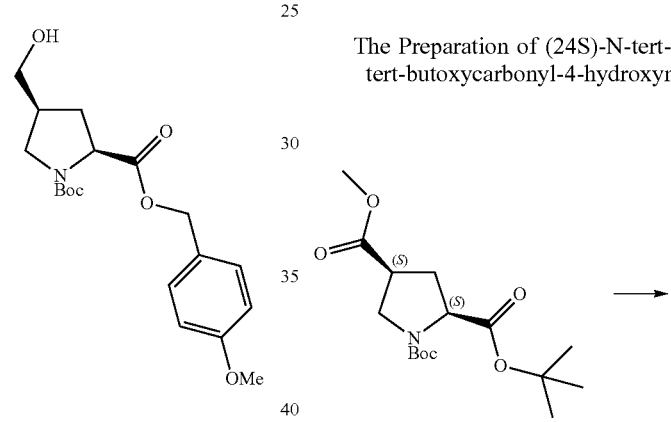

To a mixture of (2S,4S)-N-tert-butoxycarbonyl-2-tert-butoxycarbonyl-4-methoxycarbonyl pyrrolidine (2 g, 6.1 mmol) in 20 ml of isopropanol was added NaBH$_4$ (0.74 g, 20 mmol), then the mixture was stirred at 25° C. overnight, quenched by dilute HCl, extracted with ethyl acetate, then combined and concentrated the organic phase which was further purified via recrystallization by ethanol to give 1.7 g of (2S,4S)-N-tert-butoxycarbonyl-2-tert-butoxycarbonyl-4-hydroxymethylpyrrolidine as white solid in 93.2% yield, de 98.4%.

EXAMPLE 19

The Preparation of (2R,4R)-N-trimethylsilyl-2-tert-butoxycarbonyl-4-hydroxymethylpyrrolidine

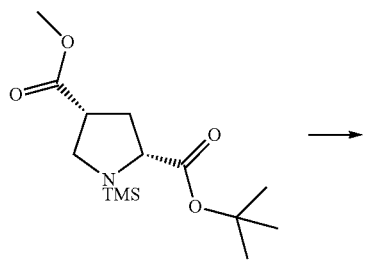

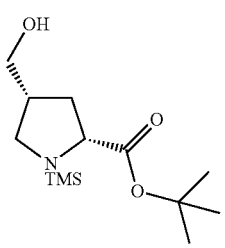

To a mixture of (2R,4R)-N-trimethylsilyl-2-tert-butoxycarbonyl-4-methoxycarbonyl pyrrolidine (2.5 g, 7.3 mmol) in 20 ml of THF was added red aluminum (4.04 g, 20 mmol), then the mixture was stirred at 25° C. overnight, quenched by dilute HCl, extracted with ethyl acetate, then the combined organic phase was concentrated, and then purified by column chromatography to give 1.59 g of (2R,4R)-N-trimethylsilyl-2-tert-butoxycarbonyl-4-hydroxymethylpyrrolidine in 79.9% yield.

EXAMPLE 19-2

The Preparation of (2R,4R)-N-trimethylsilyl-2-tert-butoxycarbonyl-4-hydroxymethylpyrrolidine

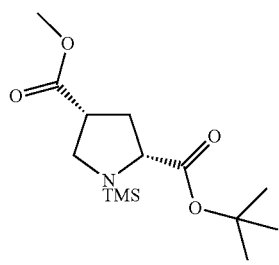

To a mixture of (2R,4R)-N-trimethylsilyl-2-tert-butoxycarbonyl-4-methoxycarbonyl pyrrolidine (2.5 g, 7.3 mmol) in 20 ml of THF was added red aluminum (4.04 g, 20 mmol), then the mixture was stirred at 25° C. overnight, quenched by dilute HCl, extracted with ethyl acetate, then combined and concentrated the organic phase which was recrystallized by ethanol to give 1.82 g of (2R,4R)-N-trimethylsilyl-2-tert-butoxycarbonyl-4-hydroxymethylpyrrolidine in 91.1% yield, de 97.9%.

EXAMPLE 20

The Preparation of (2S,4S)-N-tert-butoxycarbonyl-2-tert-butoxycarbonyl-4-hydroxymethylpyrrolidine

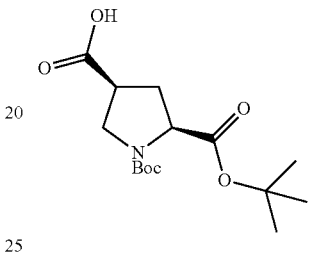

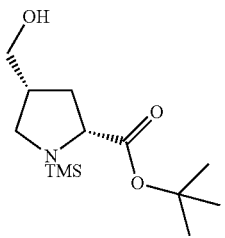

To a 100 ml of single-necked flask was added (2,4S)-N-tert-butoxycarbonyl-2-tert-butoxycarbonyl-4-carboxyl pyrrolidine (0.66 g, 2.11 mmol), TEA (0.4 ml, 2.74 mmol) and 5 ml of methylene chloride, then ethyl chloroformate (252 mg, 2.32 mmol) was added dropwise, after stirring for another 1 hour at 25° C., washed with water and organic phase was concentrated, then the residue was dissolved in THF and water, NaBH$_4$ (230 mg, 6 mmol) was added, after stirring for another 3 hours at 25° C., quenched by dilute HCl, and extracted with ethyl acetate, dried over MgSO$_4$, then filtered and evaporated to give 540 mg of (2S,4S)-N-tert-butoxycarbonyl-2-tert-butoxycarbonyl-4-hydroxymethylpyrrolidine as colorless oil in 85.2% yield.

EXAMPLE 20-2

The Preparation of N-tert-butoxycarbonyl-2-tert-butoxycarbonyl-4-hydroxymethylpyrrolidine

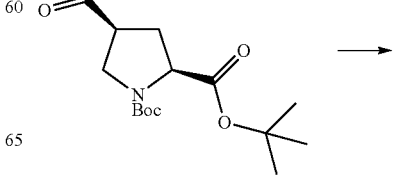

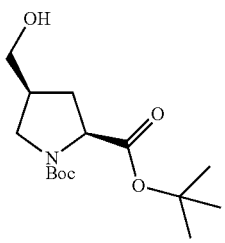

To a 100 ml of single-necked flask was added (2S,4S)-N-tert-butoxycarbonyl-2-tert-butoxycarbonyl-4-carboxyl pyrrolidine (0.66 g 2.11 mmol), TEA (0.4 ml, 2.74 mmol) and 5 ml of methylene chloride, then ethyl chloroformate (252 mg, 2.32 mmol) was added dropwise, after stirring for another 1 hour at 25° C., washed with water and organic phase was concentrated, then the residue was dissolved in THF and water, NaBH$_4$ (230 mg, 6 mmol) was added, after stirring for another 3 hours at 25° C., quenched by dilute HCl, and extracted with ethyl acetate, dried over MgSO$_4$, then filtered, evaporated and recrystallized with ethanol to give 566 mg of N-tert-butoxycarbonyl-2-tert-butoxycarbonyl-4-hydroxymethylpyrrolidine as colorless oil in 89.2%, de 97.6%.

EXAMPLE 21

The Preparation of (2S,4S)-N-tert-butoxycarbonyl-2-tert-butoxycarbonyl-4-hydroxymethyl-2,3-dihydro-1H-pyrrole

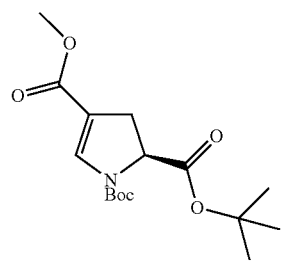

To a mixture of (2S,4S)-N-tert-butoxycarbonyl-2-tert-butoxycarbonyl-4-methoxycarbonyl 2,3-dihydro-1H-pyrrole (3 g, 9.2 mmol) dissolved in 20 ml of THF, diisobutylaluminium hydride (5.6 g, 46 mmol) was added, after stirred overnight at 25° C., quenched by dilute HCl, and extracted with ethyl acetate, concentrated, then recrystallized by ethanol to give 2.52 g of (2S,4S)-N-tert-butoxycarbonyl-2-tert-butoxycarbonyl-4-hydroxymethyl-2,3-dihydro-1H-pyrrole in 91.7% yield.

EXAMPLE 22

The Preparation of (2R,4R)-N-trimethylsilyl-2-tert-butoxycarbonyl-4-hydroxymethyl-2,3-dihydro-1H-pyrrole

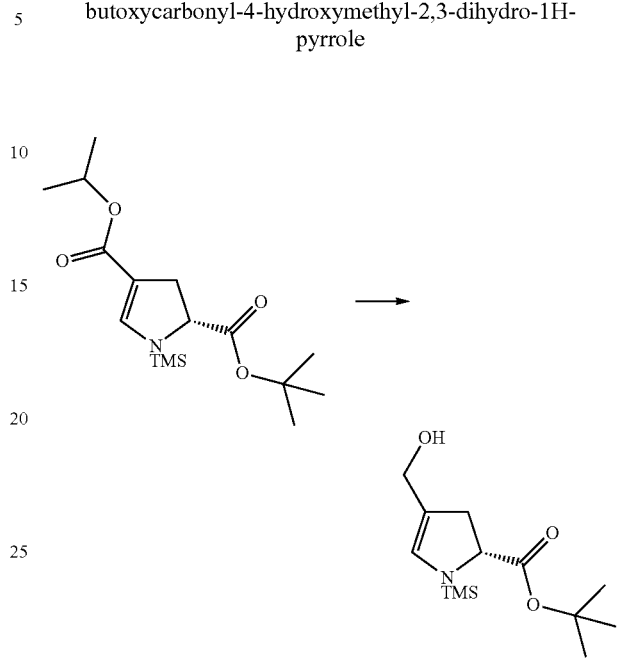

To a mixture of (2R,4R)-N-trimethylsilyl-2,4-di(tert-butoxycarbonyl)-2,3-dihydro-1H-pyrrole (1.9 g, 5.9 mmol) in 20 ml of THF, red aluminum (5.7 g, 28 mmol) was added, after stirring overnight at 25° C., quenched by dilute HCl, and extracted with ethyl acetate, then purified by column chromatography to give 1.08 g of (2R,4R)-N-trimethylsilyl-2-tert-butoxycarbonyl-4-hydroxymethyl-2,3-dihydro-1H-pyrrole as oil in 67.5% yield.

EXAMPLE 23

The Preparation of (2S,4S)-N-tert-butoxycarbonyl-2-carboxyl-4-hydroxymethylpyrrolidine

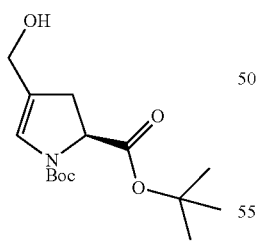 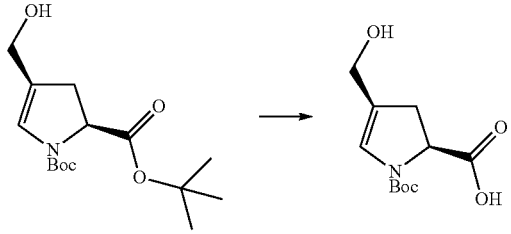

(2S,4S)-N-tert-butoxycarbonyl-2-tert-butoxycarbonyl-4-hydroxymethylpyrrolidine (3 g, 10 mmol) was dissolved in 20 ml of hydrochloride ethanol solution. After stirring for 3 hours at 25° C., the solvent was evaporated, then 15% NaOH and (Boc)$_2$O (3.27 g, 1.5 eq) were added, stirred for 3 hours, and extracted with ethyl acetate, then adjusted to PH=2, extracted with ethyl acetate again, concentrated to give 2.2 g of white solid in 89.7% yield.

EXAMPLE 24

The Preparation of (2R,4R)-2-carboxyl-4-hydroxymethylpyrrolidine

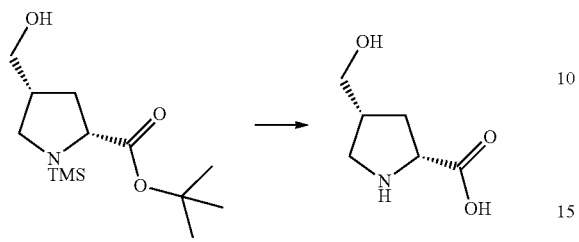

(2R,4R)-N-trimethylsilyl-2-tert-butoxycarbonyl-4-hydroxymethylpyrrolidine (2.7 g, 10 mmol) was dissolved in 20 ml of hydrochloride ethanol solution. After stirring for 3 hours at 25° C., the solvent was evaporated to give 1.2 g of (2R,4R)-2-carboxyl-4-hydroxymethylpyrrolidine in 82.7% yield.

EXAMPLE 25

The Preparation of (2S,4S)-N-tert-butoxycarbonyl-2-carboxyl-4-hydroxymethylpyrrolidine

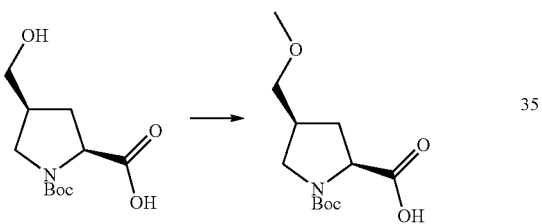

(2S,4S)-N-tert-butoxycarbonyl-2-carboxyl-4-hydroxymethylpyrrolidine (2.45 g, 10 mmol) was dissolved in 50% of NaOH, then methyl iodide (4.26 g, 0 mmol) was added, after stirring for 3 hours at 2° C., the resulting mixture was extracted with ethyl acetate, then adjusted to PH=2, extracted with ethyl acetate, the organic phase was washed with water, dried over MgSO₄, concentrated to give 2.5 g of white solid in 96.5% yield.

EXAMPLE 26

The Preparation of (2S,4S)-N-tert-butoxycarbonyl-2-tert-butoxycarbonyl-4-hydroxymethylpyrrolidine

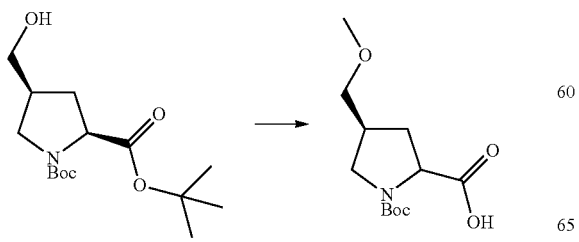

(2S,4S)-N-tert-butoxycarbonyl-2-tert-butoxycarbonyl-4-hydroxymethylpyrrolidine (3.0 g, 10 mmol) was dissolved in 50% of NaOH, then methyl iodide (4.26 g, 0 mmol) was added. After stirring for 3 hours at 25° C., the resulting mixture was extracted with ethyl acetate, then adjusted to PH=2, extracted with ethyl acetate, and the organic phase was washed with water, dried over MgSO₄, and concentrated to give 2.5 g of white solid in 96.5% yield.

EXAMPLE 26-2

The Preparation of (2S,4S)-N-tert-butoxycarbonyl-2-tert-butoxycarbonyl-4-methoxymethylpyrrolidine

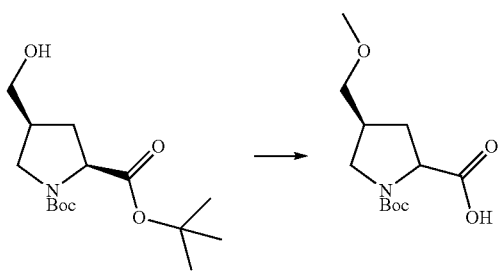 [SMILES: CC(C)(C)OC(=O)[C@@H]1C[C@H](CO)CN1C(=O)OC(C)(C)C ; COC[C@H]1CC(C(=O)O)N(C(=O)OC(C)(C)C)C1]

To a mixture of (2S,4S)-N-tert-butoxycarbonyl-2-tert-butoxycarbonyl-4-hydroxymethylpyrrolidine (3.0 g, 10 mmol) in ethyl acetate, Bu₄NBr (0.65 g, 2 mmol) and methyl sulphate (2.5 g, 20 mmol) were added, after dissolving completely, 2 g of NaOH solution (40%) was added dropwise with maintaining the inner temperature at −5° C. to 5° C. After the addition, the mixture was maintained at this temperature for 3 hours, and extracted with ethyl acetate, and then the organic phase was washed with dilute HCl aqueous solution and dilute NaOH aqueous solution respectively. The organic solvent was concentrated then recrystallized by hexane to give 2.47 g of white solid in 95.2% yield.

EXAMPLE 27

The Preparation of (2S,4S)-2,4-dicarboxyl pyrroldine

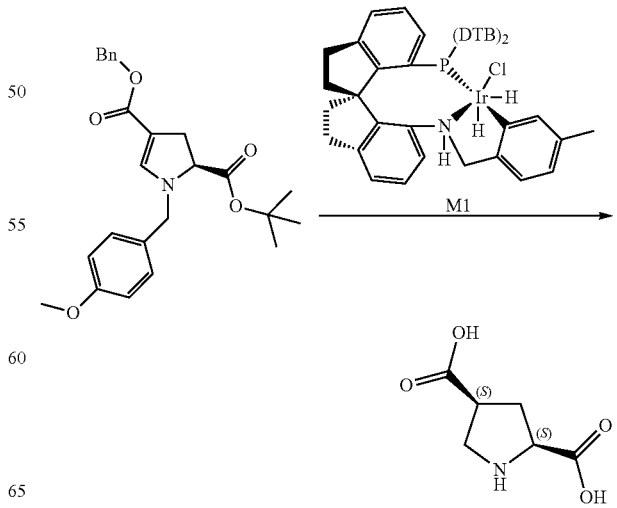

Chiral catalyst M (7.0 mg, 0.007 mmol), EtONa (38 mg, 0.71 mmol) and (S)-N-p-methoxybenzyl-2-tert-butoxycarbonyl-4-benzyloxycarbonyl-2,3-dihydro-1H-pyrrole (3 g, 7.1 mmol) were weighted into a reaction inner tube under the protection of N₂ atmosphere, then 15 ml of ethanol and 3 ml of DMF were added. The reaction tube was placed into an autoclave. The original atmosphere was displaced with hydrogen atmosphere. The hydrogen pressure inside the autoclave was ultimately maintained at 1.4-1.5 MPa and then heated to 50° C. in an oil bath with reacting for 3 h. Starting material was consumed completely until the inside pressure did not continue to decrease, then the reaction was stopped and the resulting mixture was concentrated. 30 ml of water and 30 ml of ethyl acetate were added, and aqueous phase was extracted with ethyl acetate (2×20 ml). the combined organic phase was washed with saturated brine, dried over MgSO₄, filtered and concentrated to give 1.0 g of (2S,4S)-2,4-dicarboxyl pyrrolidine in 88.6% yield. The product was analyzed by chiral HPLC, the chiral purity is 97.5% de.

EXAMPLE 28

The Preparation of (S)-1-benzyl-5-methyl-2-((tert-butoxycarbonyl)amino)pentanedioate

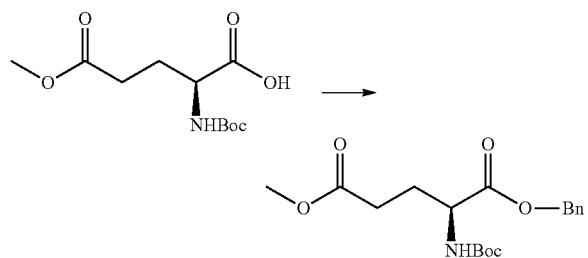

To a 100 ml of single-necked bottle was added (S)-5-methyl-2-((tert-butoxycarbonyl)amino)pentanedioate (7.8 g, 24.6 mmol), benzyl chloride (3.4 g, 27 mmol), K₂CO₃ (3.1 g, 29.5 mmol) and 30 ml of DMF, the mixture was maintained at 40 to 60° C. for 6 hours, after the completion of the reaction, the solvent was evaporated, extracted with methyl tert-butyl ether after the addition of water, and then the organic phase was evaporated to dryness to give 8.45 g of (S)-1-benzyl-5-methyl-2-((tert-butoxycarbonyl)amino)pentanedioate as light yellow oil in 97.9% yield.

EXAMPLE 29

The Preparation of (S)-N-tert-butoxycarbonyl-2-benzyloxycarbonyl-2,3-dihydro-1H-pyrrole

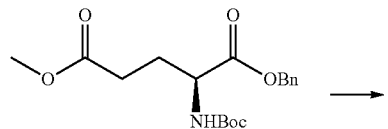

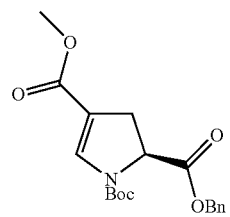

To a 250 ml of three-necked bottle was added 60 ml of LHMDS (7.6 g, 45.4 mmol) under the protection of nitrogen, then cooled to −70° C. to −78° C., after the addition of (S)1-benzyl-5-methyl-2-(tert-butoxycarbonyl)amino pentanedioate (8.0 g, 25.2 mmol) in 40 m of THF, the mixture was maintained at this temperature for 1 hour, then ethyl formate (4.4 g, 60 mmol) was added dropwise slowly and the inner temperature was maintained below −70° C. After the addition, the mixture was maintained at this temperature for 8 hours. After the completion of the reaction, the reaction solution was warmed to about −40° C., 3.5 ml of acetic acid was added, and then quenched with 30 ml of water, extracted with ethyl acetate, dried over MgSO₄, filtered and concentrated to give a light yellow oil. Then the above mentioned oil was dissolved in methylene chloride. After the addition of TFA (3.16 g, 27.7 mmol), the mixture was stirred for 4 hours at 25° C., then concentrated to dryness to give 8.8 g of (S)-N-tert-butoxycarbonyl-2-benzyloxycarbonyl-4-methoxycarbonyl-2,3-dihydro-1H-pyrrole in 96.7% yield.

EXAMPLE 30

The Preparation of (2S,4S)-2-carboxyl-4-methoxycarbonyl pyrrolidine

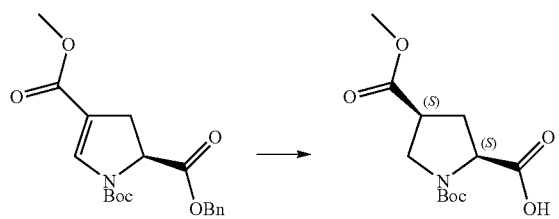

To a 100 ml of single-necked bottle was added (S)-N-tert-butoxycarbonyl-2-benzyloxycarbonyl-4-methoxycarbonyl-2,3-dihydro-1H-pyrrole (3.0 g, 8.3 mmol) (prepared by the method of Example 5), 10% wet Pd/C (0.7 g, 30%), one drop of acetic acid and 5 ml of Methanol, then the mixture was stirred at 25° C. overnight, after filtration and evaporation, 2.27 g of (2S,4S)-2-carboxyl-4-methoxycarbonyl pyrrolidine as colorless oil was obtained in 100% yield, de 98.8%.

EXAMPLE 31

The Preparation of (2S,4S)-N-tert-butoxycarbonyl-2-tert-butoxycarbonyl-4-hydroxymethylpyrrolidine

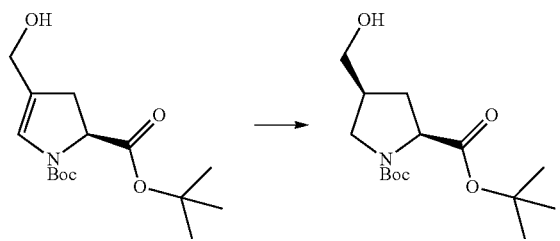 [SMILES: CC(C)(C)OC(=O)[C@@H]1CC(CO)=CN1C(=O)OC(C)(C)C ; CC(C)(C)OC(=O)[C@@H]1C[C@H](CO)CN1C(=O)OC(C)(C)C]

The procedure of example 15 was repeated to afford (2S,4S)-N-tert-butoxycarbonyl-2-tert-butoxycarbonyl-4-hydroxymethylpyrrolidine containing (2S 4R)-N-tert-butoxycarbonyl-2-tert-butoxycarbonyl-4-hydroxymethylpyrrolidine, de 61.1%%.

EXAMPLE 32

The Preparation of (2R,4R)-N-trimethylsilyl-2-tert-butoxycarbonyl-4-hydroxymethylpyrrolidine

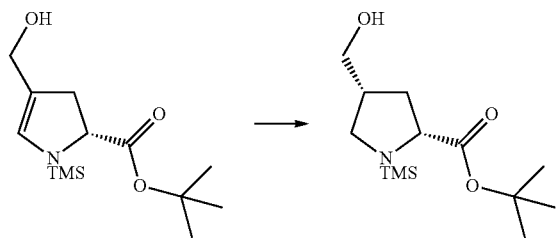

The procedure of example 15 was repeated to afford (2R,4R)-N-trimethylsilyl-2-tert-butoxycarbonyl-4-hydroxymethylpyrrolidine containing (2R,4S)-N-trimethylsilyl-2-tert-butoxycarbonyl-4-hydroxymethylpyrrolidine, de 55.4%.

COMPARISON EXAMPLE 1

The Preparation of (2S)-2,4-dimethoxycarbonyl pyrrolidine

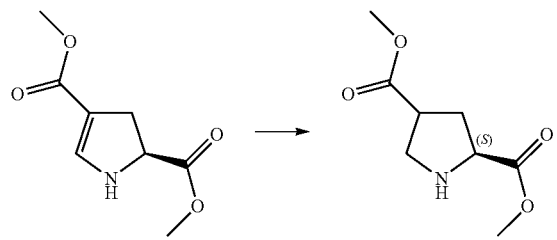

To a 100 ml of single-necked bottle was added (S)-2,4-dimethoxycarbonyl-2,3-dihydro-1H-pyrrole (1.85 g, 10 mmol), 10% wet Pd/C (0.7 g, 30%), one drop of acetic acid and 5 ml of methanol, then the mixture was stirred at 25° C. overnight, after filtration and evaporation, 1.80 g of (2S)-2,4-dimethoxycarbonyl pyrrolidine as colorless oil was obtained in 96.2% yield.

Thus it can be seen from the comparison example that, the product (2S)-2,4-dimethoxycarbonyl pyrrolidine is racemic at 4 position.

The experimental results presented below are got in accordance with example 6 when $R_1$, $R_3$, $P_1$ are different substituents.

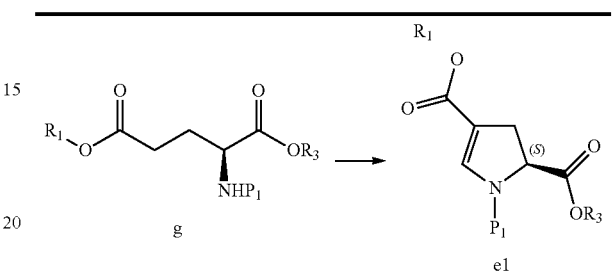

| Product | $R_1$ | $R_3$ | $P_1$ | Yield |
|---|---|---|---|---|
| e1-1 | methyl | t-Bu | trifluoroacetyl | 73.2% |
| e1-2 | methyl | t-Bu | allyloxycarbonyl | 77.0% |
| e1-3 | methyl | t-Bu | triphenylmethyl | 80.4% |
| e1-4 | methyl | t-Bu | benzyl | 85.7% |
| e1-5 | methyl | t-Bu | Cbz | 90.1% |
| e1-6 | methyl | t-Bu | p-chlorobenzyl | 87.6% |
| e1-7 | isopropyl | t-Bu | Boc | 85.1% |
| e1-8 | isopropyl | t-Bu | Cbz | 84.2% |
| e1-9 | isopropyl | t-Bu | benzyl | 82.2% |
| e1-10 | n-hexyl | t-Bu | Boc | 61.3% |
| e1-11 | methyl | benzyl | benzyl | 86.7% |
| e1-12 | methyl | benzyl | p-chlorobenzyl | 88.9% |
| e1-13 | methyl | benzyl | Cbz | 94.3% |
| e1-14 | isopropyl | benzyl | Boc | 74.7% |
| e1-15 | methyl | isopropyl | Boc | 78.7% |
| e1-16 | methyl | n-hexyl | Boc | 70.0% |
| e1-17 | methyl | p-nitrobenzyl | Boc | 83.5% |
| e1-18 | methyl | ethyl | Boc | 86.9% |
| e1-19 | benzyl | t-Bu | Boc | 88.8% |

The experimental results presented below are got in accordance with example 6 in the presence of different reaction reagents.

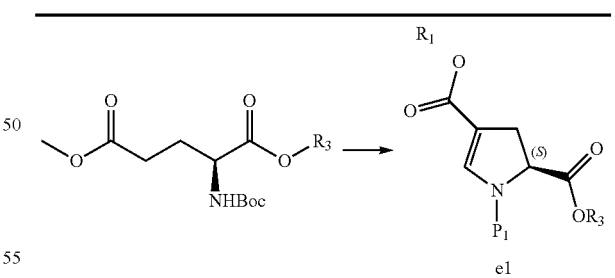

| Product | $R_3$ | base | formic mixed anhydride/alkyl formate | Yield |
|---|---|---|---|---|
| e1-20 | t-Bu | lithium bis(trimethylsilyl)amide | formic anhydride | 85.3% |
| | t-Bu | lithium bis(trimethylsilyl)amide | pivalic formic anhydride | 78.0% |
| | t-Bu | lithium bis(trimethylsilyl)amide | benzoic formic anhydride | 73.5% |
| | t-Bu | lithium diisopropylamide | formic anhydride | 79.1% |

-continued

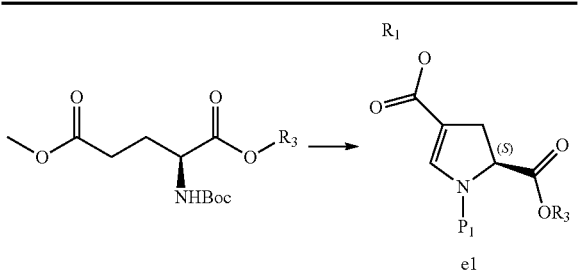

| Product | $R_3$ | base | formic mixed anhydride/ alkyl formate | Yield |
|---|---|---|---|---|
| | t-Bu | lithium diisopropylamide | acetic formic anhydride | 86.7% |
| | t-Bu | lithium diisopropylamide | pivalic formic anhydride | 71.9% |
| | t-Bu | sodium ethoxide | acetic formic anhydride | 86.9% |
| | t-Bu | sodium propoxide | acetic formic anhydride | 87.2% |
| | t-Bu | lithium bis(trimethylsilyl)amide | ethyl formate | 94.8% |
| | t-Bu | sodium methoxide | pivalic formic anhydride | 67.2% |
| | t-Bu | sodium methoxide | n-propylformate | 65.9% |
| e1-21 | benzyl | lithium bis(trimethylsilyl)amide | formic anhydride | 82.5% |
| | benzyl | lithium bis(trimethylsilyl)amide | pivalic formic anhydride | 78.7% |
| | benzyl | lithium bis(trimethylsiyl)amide | benzoic formic anhydride | 70.3% |
| | benzyl | lithium bis(trimethylsilyl)amide | acetic formic anhydride | 96.6% |
| | benzyl | lithium bis(trimethylsilyl)amide | methyl formate | 84.5% |
| | benzyl | lithium bis(trimethylsilyl)amide | n-propylformate | 85.7% |
| | benzyl | n-butyllithium | acetic formic anhydride | 89.1% |
| | benzyl | n-butyllithium | ethyl formate | 87.4% |
| | benzyl | sodium methoxide | acetic formic anhydride | 90.9% |
| | benzyl | sodium methoxide | ethyl formate | 89.7% |
| | benzyl | sodium methoxide | methyl formate | 70.4% |
| | benzyl | potassium isopropoxide | benzoic formic anhydride | 63.0% |
| | benzyl | potassium isopropoxide | n-propylformate | 68.1% |
| | benzyl | sodium hydride | ethyl formate | 79.8% |
| | benzyl | sodium hydride | methyl formate | 63.6% |
| | benzyl | sodium isopropoxide | pivalic formic anhydride | 70.2% |

The experimental results presented below are got in accordance with example 10 when $R_5$, $R_6$, $P_2$ are different substitutions.

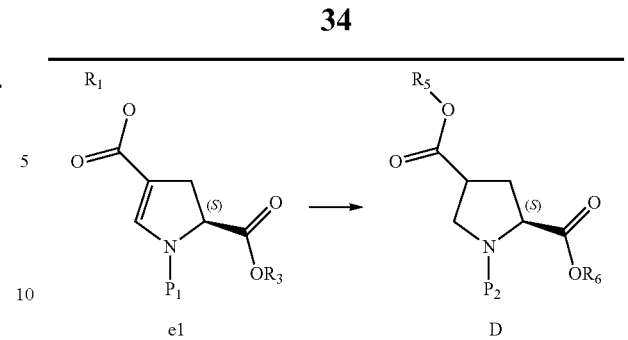

| Substrate | Product | $R_5$ | $R_6$ | $P_2$ | Yield | ee (4S) |
|---|---|---|---|---|---|---|
| e1-1 | D-1 | methyl | t-Bu | trifluoroacetyl | 97.8% | 97.2% |
| e1-2 | D-2 | methyl | t-Bu | allyloxycarbonyl | 60.1% | 95.7% |
| e1-3 | D-3 | methyl | t-Bu | H | 83.6% | 96.2% |
| e1-4 | D-4 | methyl | t-Bu | H | 100% | 97.6% |
| e1-5 | D-5 | methyl | t-Bu | Cbz | 100% | 97.7% |
| e1-6 | D-6 | methyl | t-Bu | H | 100% | 98.8% |
| e1-7 | D-7 | isopropyl | t-Bu | Boc | 100% | 91.9% |
| e1-8 | D-8 | isopropyl | t-Bu | Cbz | 100% | 91.2% |
| e1-9 | D-9 | isopropyl | t-Bu | H | 100% | 89.7% |
| e1-10 | D-10 | n-hexyl | t-Bu | Boc | 100% | 78.7% |
| e1-11 | D-11 | methyl | H | H | 100% | 96.8% |
| e1-12 | D-12 | methyl | H | H | 98.8% | 96.9% |
| e1-13 | D-13 | methyl | H | Cbz | 100% | 97.9% |
| e1-14 | D-14 | isopropyl | H | Boc | 100% | 89.1% |
| e1-15 | D-15 | methyl | isopropyl | Boc | 100% | 80.3% |
| e1-16 | D-16 | methyl | n-hexyl | Boc | 100% | 89.7% |
| e1-17 | D-17 | methyl | H | Boc | 99.0% | 98.2% |
| e1-18 | D-18 | methyl | ethyl | Boc | 100% | 65.3% |
| e1-19 | D-19 | H | t-Bu | Boc | 100% | 56.9% |

The invention claimed is:

1. A compound of formula (E),

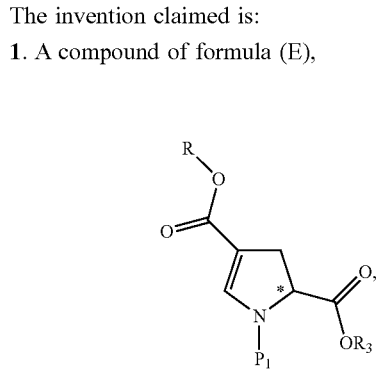

wherein R is $R_1$ or $R_2$, $R_1$ is $C_1$-$C_6$ alkyl, benzyl, p-methoxybenzyl or p-nitrobenzyl, $R_2$ is a hydrogen atom;

$R_3$ is a protecting group for carboxyl;

$P_1$ is an amino protecting group.

2. The compound according to claim 1, wherein, $R_1$ is $C_1$-$C_6$ alkyl, $R_3$ is tert-butyl, benzyl, p-methoxybenzyl or p-nitrobenzyl; $P_1$ is t-butyloxycarbonyl, p-methoxybenzyl ortbenzyloxycarbonyl.

3. The compound according to claim 2, wherein, $R_1$ is methyl, $R_3$ is tert-butyl or benzyl $P_1$ is t-butyloxycarbonyl.

4. A method for preparing the compound of formula (E) according to claim 1, wherein, obtained by reacting the compound of formula (g) through cyclization reaction,

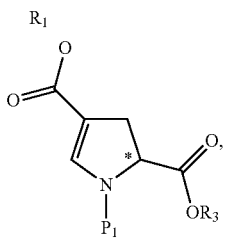

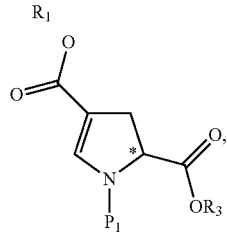

wherein $R_1$, $R_3$ and $P_1$ are as defined in claim 1.

10. A process of making a compound of formula (D), wherein, obtained by reacting the compound of formula (E) through catalytic hydrogenation,

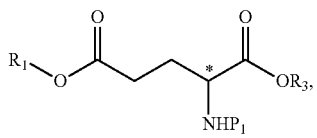

wherein the compound of formula (E) is a compound (e1).

5. The method according to claim 4, wherein, the reagent employed in the process of cyclization reaction is base/formic mixed anhydride or alkyl formate/acid.

6. The method according to claim 5, wherein, the base is lithium bis(trimethylsilyl)amide.

7. The method according to claim 5, wherein, the formic mixed anhydride is acetic formic anhydride; the alkyl formate is ethyl formate.

8. The method according to claim 4, wherein, the said compound of formula (g) being prepared by reacting the compound of formula (h) with $(R_3CO)_2$ or $R_3X$ in the presence of a base,

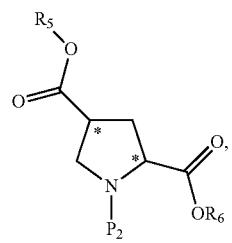

wherein $R_5$ is a hydrogen atom or $C_1$-$C_6$ alkyl;

$R_6$ is a hydrogen atom, n-propyl, isopropyl, n-butyl, isobutyl, tert-butyl, n-pentyl or n-hexyl;

$P_2$ is a hydrogen atom, acetyl, trifluoroacetyl, allyloxycarbonyl, t-butyloxycarboryl, trimethylsilyl, tert-butyldimethylsilyl or benzoyl.

11. The method according to claim 10, wherein, the catalyst for catalytic hydrogenation may be selected from palladium on carbon, platinum oxide or Raney Ni.

12. The method according to claim 10, wherein, the obtained compound formula (D) further being reduced to prepare the compound of formula (c1),

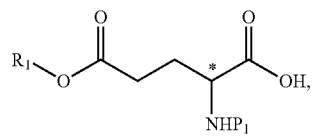

wherein $R_1$, $R_3$ and $P_1$ are as defined in claim 1, X is a halogen atom.

9. A method for preparing the compound of formula (e2), wherein, obtained by reacting the compound of formula (e1) through hydrolyzation reaction, the reagent employed for the hydrolysis is alkali base,

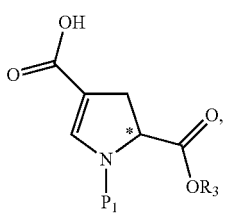

wherein $R_6$ and $P_2$ areas defined in claim 10.

13. The method according to claim 12, wherein, the reducing reagent employed is selected from tributyltin hydride, triphenyltin hydride, triethylsilicane, trichlorosilane, sodium borohydride, sodium trimethoxyborohydride, lithium tri-sec-butylhydridoborate, potassium tri-sec-butylborohydride, lithium triethylborohydride, diisobutylaluminium hydride and sodium bis(2-methoxyethoxy)aluminiumhydride.

14. The method according to claim 10, wherein, when $R_5$ is a hydrogen atom, further comprising the addition of alkyl chloroformate before the step of subjecting the carboxyl group of compound (D) to reduction reaction.

15. The method according to claim 12, wherein, the obtained compound of formula (c1) further being converted to the compound of formula (b1) by removing the carboxyl group,

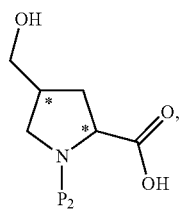

b1 wherein $P_2$ is as defined in claim 10.

16. The method according claim 15, wherein, the obtained compound of formula (b1) further being converted to the compound of formula (A1) by alkylation reaction,

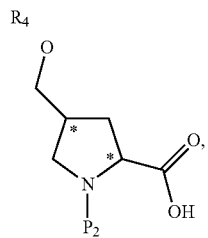

A1 wherein $R_4$ is $C_1$-$C_6$ allkyl, $P_2$ is as defined in claim 10.

17. The method according to claim 5, wherein, the base is selected from lithium bis(trimethylsily)amide, lithium diisopropylamide, n-butyllithium, sodium alcoholate and potassium alcoholate; the formic mixed anhydride is selected from acetic formic anhydride, formic pivalic anhydride and formic benzoic anhydride; the acid is selected from trifluoroacetic acid and acetic acid, the alkyl formate is selected from methyl formate, ethyl formate, propyl formate.

* * * * *